United States Patent [19]

Jackson

[11] Patent Number: 4,621,729
[45] Date of Patent: Nov. 11, 1986

[54] PATIENT MEDICAL INFORMATION AND EDUCATION CONTAINER

[75] Inventor: Frank W. Jackson, Mechanicsburg, Pa.

[73] Assignee: J N Associates, Camp Hill, Pa.

[21] Appl. No.: 691,333

[22] Filed: Jan. 14, 1985

[51] Int. Cl.⁴ .................. B65D 27/08; B65D 27/06
[52] U.S. Cl. .................................. 206/37; 206/232; 206/38; 150/147
[58] Field of Search .............. 206/37, 38, 216, 232; 150/147, 149, 132

[56] References Cited

U.S. PATENT DOCUMENTS

| | | | |
|---|---|---|---|
| 1,017,006 | 2/1912 | Lee | 206/232 |
| 1,037,264 | 9/1912 | Kimmel | 150/147 |
| 1,677,770 | 7/1928 | Harnsberger | 206/232 |
| 1,893,397 | 1/1933 | Buxton | 150/149 |
| 2,737,991 | 3/1956 | Bass | 150/147 |
| 2,851,284 | 9/1958 | Copen | 150/132 |
| 3,347,358 | 10/1967 | Meyers | 206/232 |
| 3,402,808 | 9/1968 | Yannuzzi | 206/232 |
| 3,655,119 | 4/1972 | Thompson | 206/37 |
| 3,792,542 | 2/1974 | Cohan | 206/37 |
| 3,958,690 | 5/1976 | Gee, Sr. | 206/232 |
| 4,016,664 | 4/1977 | Kaufmann | 150/147 |
| 4,189,053 | 2/1980 | Stagnitto et al. | 206/232 |
| 4,216,979 | 8/1980 | Janik | 150/147 |

FOREIGN PATENT DOCUMENTS 44018   7/1908   Switzerland .............. 206/216

Primary Examiner—William Price
Assistant Examiner—Brenda Ehrhardt
Attorney, Agent, or Firm—Eugene Chovanes

[57] ABSTRACT

A patient medical information and education container which includes a strip of material divided into a plurality of panels hingedly connected one with another whereby the panels can be folded one upon another to form a container of relatively small dimensions, the strip including a pocket on one of the panels adapted to contain cards including, on one face, medicine nature and suggestions concerning recommended use thereof by a patient for optimal results, the opposite side preferably will include cautioning of use, such as alerting the patient regarding possible side effects, the various panels including indicia indicating material of significance in current or future treatment of a patient by the use of certain medicines and under certain conditions of treatment thereof.

2 Claims, 7 Drawing Figures

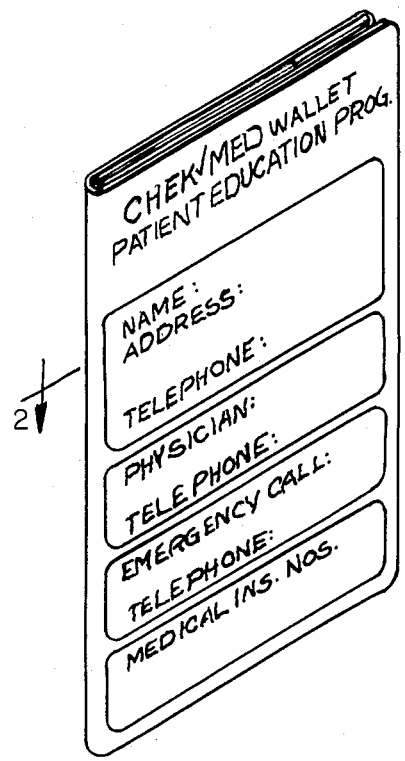
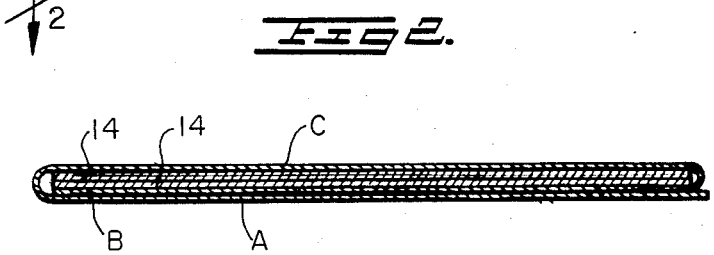
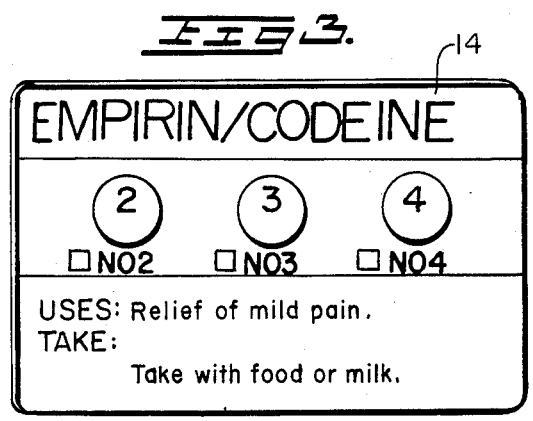
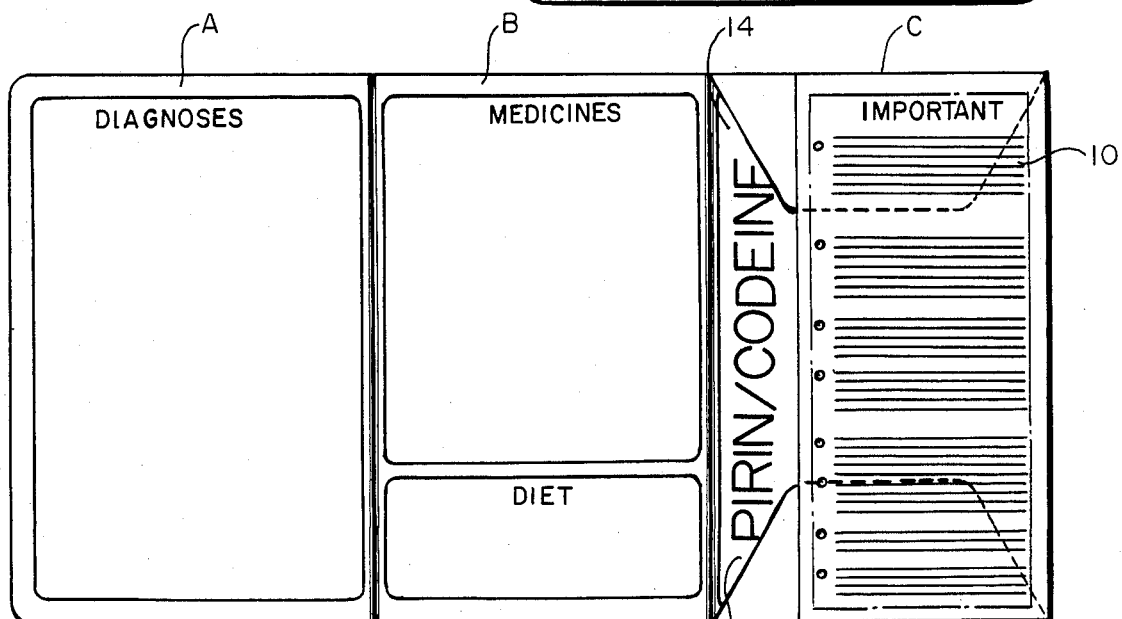

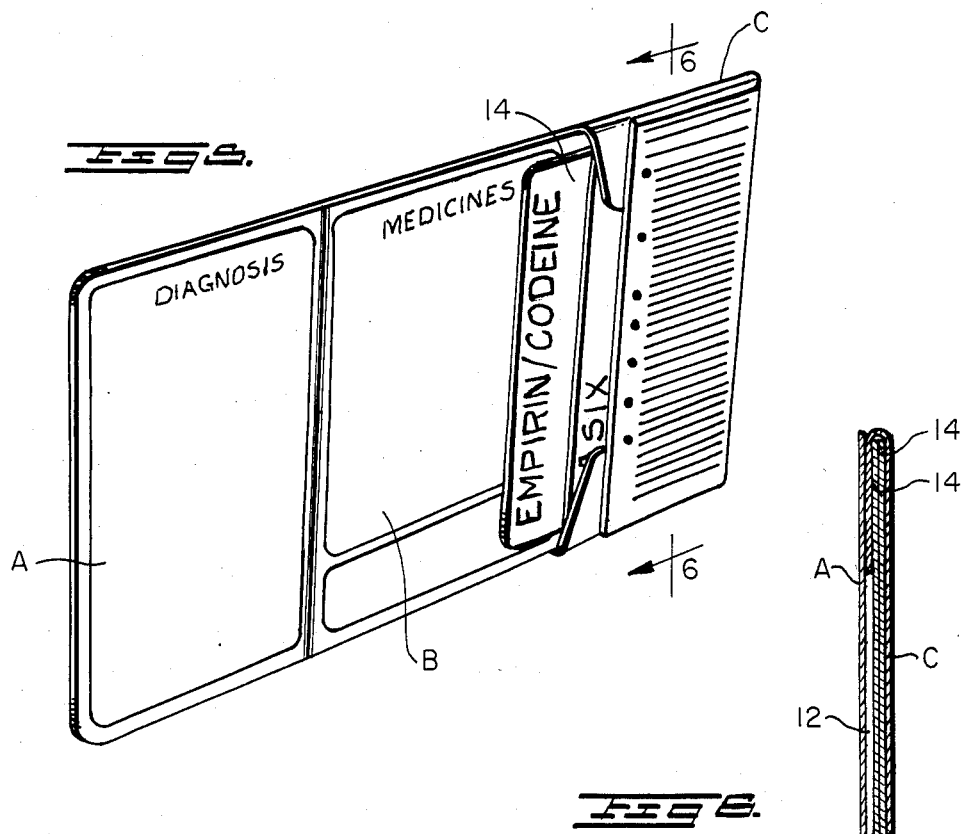
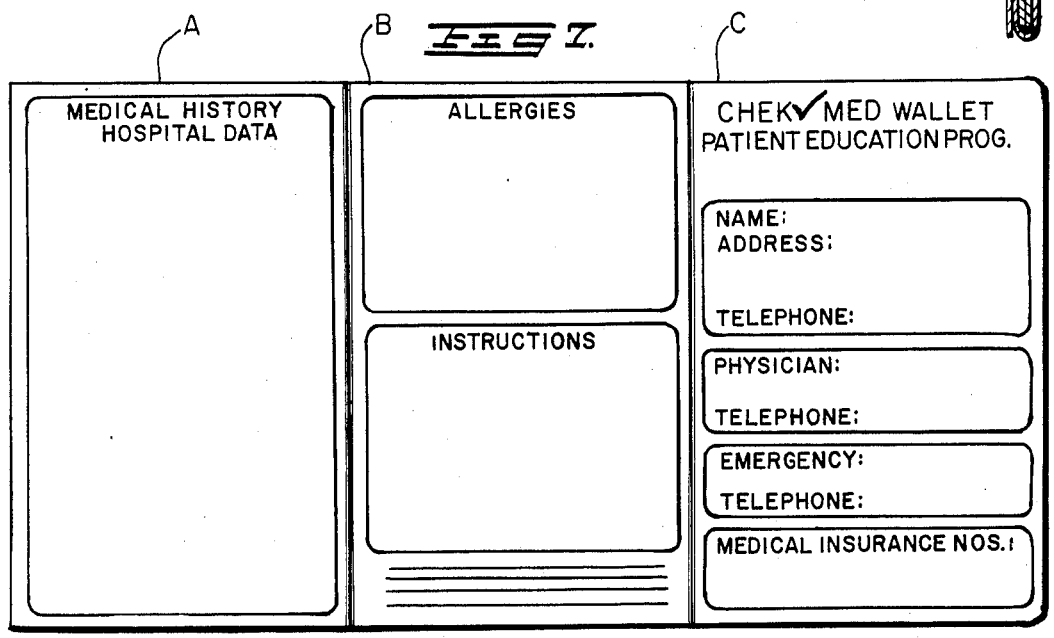

PATIENT MEDICAL INFORMATION AND EDUCATION CONTAINER

BACKGROUND OF THE INVENTION

It is often necessary to provide either a patient, or a doctor who may be new to the patient, with information relative to such patient's health condition and any prior or existing treatment relative to such condition. This information needs to be comprehensive, accurate, and as complete as possible. It should include such facts as the patient's name, address, telephone number, names and telephone numbers of prior or personal physicians, as well as emergency telephone numbers, medical insurance numbers and any information related to pre-existing conditions for which the patient has been treated. Also, it should include prior diagnosis, medicines prescribed and currently being used by the patient, diets prescribed for the patient, medical history and current hospital data. Any allergies which the patient might have should be revealed, and detailed instructions previously given to the patient with reference to his condition as well as prescribed treatments, should be made known.

Relying on memory to supply this information is risky and, in some instances, results either in failure to supply correct information, or omission of pertinent information which would be of assistance to a treating physician. Such errors or omissions could be of vital importance to a patient's treatment.

A patient frequently will experience a job related move, either temporary or permanent, from a location in which the patient was being treated by a previous physician to a new location and the necessity arises of providing any new physician with all pertinent information concerning the patient, his maladies or sicknesses and the current treatment which had been provided in the old location.

Work related or pleasure travel have also provided conditions where a patient on a trip, for example, is confronted with an occurrence related to his physical condition and/or previous treatment. Here again, information which is preferably in some form such as a written description of the various features and aspects as hereinbefore described should be available readily, even including situations where the patient is personally not in a condition to pass this information on to a treating agency or physician. Additionally, older patients frequently are unclear as to their medications, and the present invention assists them in supplying the right information, and aids medical personnel in providing proper care to such patients.

The present invention teaches a patient medical information and education program and container which preferably is in easily conveyable form, such as wallet size, so the patient can carry it on his person, to provide the most complete information concerning the patient to either a succeeding physician or to a person or persons confronted with an occurrence or accident which prevents the patient from transmitting this information.

It is also a well known fact that an attempt to carry all of this significant information in one's memory for transferring to another person presents a serious risk of overlooking some factors or information which otherwise could be of substantial help to treating persons under all circumstances which might be present.

It is accordingly an important object of the present invention to overcome such aforementioned difficulties so that a patient can be more quickly treated by one to whom the previous information is available and in some circumstances this information, as transmitted, might even be used in saving a patient's life by eliminating time-consuming diagnosis and/or other factors which might affect treatment of the patient.

It is a further object of the invention to provide, in simplicity and detail, to the patient such information pertaining to any physical condition he might have warranting treatment as also to incorporate instructions to the patient as to any restrictions or suggestions on his actions and to indicate when and how much of a prescribed medicine should be taken. The latter information is of substantial interest for a new physician with reference to a patient or to facts arising in an emergency situation.

It is a further object of the invention by use of drug-identification cards, to alert a patient regarding possible side effects of a specific drug, and to offer suggestions for lessening or eliminating such possible side effects, and recommendations as to recognizing any serious reaction.

Apropos of this situation, it is interesting to note steps which have been taken by pharmacists and pharmacy groups to improve patient use of medicine and a prescribed dosage thereof, as well as a failure to partake of a medicine at a prescribed time interval. In this connection, it is to be noted that current literature indicates that more than 1.5 billion prescriptions are dispensed every year in the United States, but that many are not used properly according to medical authorities. A newspaper article to this effect is contained in the WASHINGTON POST Newspaper of Saturday, Aug. 18, 1984, on page D1.

It is also known that currently manufacturers and distributors of medicine are including detailed information on medicines, peculiarities and usages thereof, in literature made available to the medical industry and such information is normally enclosed in containers of a medicine as shipped to pharmacies in order to indicate valuable information for the use of the pharmacist as also conditions of use to a patient. This literature, however, is normally retained by a pharmacist and is not transmitted to a patient for whom a prescription is filled. It is a still further object of this invention to attempt to alleviate this lack of information transmittal to a patient.

Apropros of this, for some medicines, information concerning the same is placed on individual cards adapted for transmittal to a patient and containing details of the medication and its use and possible problems which could occur in usage of the medicine, dependent upon a patient's physical being, or reaction to a particular substance.

While the present invention will be specifically described in a single preferred form of construction, obviously the invention is not limited to this specific structure and variations in specifics of details of construction will be obvious and within the scope of the invention as defined by the claims herein.

BRIEF DESCRIPTION OF THE DRAWINGS

The accompanying drawings illustrate a preferred embodiment of the invention, and when taken together with the following description, serve to explain the principles and structure of the invention.

In the drawings:

FIG. 1 is a perspective view of the article of the present invention in a closed condition such as when being carried by a patient which might be in a wallet, purse or the like;

FIG. 2 is a cross-sectional view of the article of the invention taken on line 2—2 of FIG. 1;

FIG. 3 is a pictorial plan view of one card as mentioned above containing information concerning a particular medicine and which is adapted to be removably contained in the container of the present invention, it being understood that a plurality of such cards can be and are intended to be so disposed as to be readily available to the patient and/or other personnel of interest;

FIG. 4 is a plan view of the container utilized in the present invention showing it in an open and extended form and disclosing designated portions thereof to include material information of significance;

FIG. 5 is a perspective view of the device shown in FIG. 4, in perspective, and disclosing one informational card partially removed from a pocket formed and constituted as a portion of the package;

FIG. 6 is a sectional view through the pocket area of FIG. 5; and

FIG. 7 is a plan view similar to FIG. 4 but disclosing the opposite side of the unit and containing areas and designations to contain additional information.

DESCRIPTION OF THE PREFERRED EMBODIMENT

Referring now specifically to the drawings, the article of the present invention is composed of, preferably, an elongated sheet of material such as paper or thin cardboard or plastic. As will be seen from FIGS. 4, 5 and 7, there are a plurality of sections or panels formed by a folding procedure at points or lines provided in the sheet for that purpose and to permit a retraction and/or folded condition of the container such as when carried by or with a patient. This closed position or condition is shown in FIG. 1 of the drawings. The outer sheet or member of the article consists of three panels designated A, B and C, in FIG. 4. The folded condition is shown in FIG. 1. It is obvious that the sections or panels A, B and C are foldable from the condition shown in FIG. 4 to that shown in FIG. 1 for purposes of carrying or transmittal with or by a patient.

The internal sides of the panels or sections, use and construction thereof, are broadly shown in FIG. 4 and which will be described in greater detail hereinafter. FIG. 1 and FIG. 7 conjointly disclose the outer sides or faces of the panels A, B and C and also indicia, as on the interior of the panels, spelling out a preferred informational reciting area.

The informational receiving panels are adapted to include sufficient details and instructions to aid either the patient and/or a treating person.

Reference is here made to FIG. 7 which discloses the external side of the panel. The panel A includes a data recording heading "Medical History Hospital Data" and it is the purpose of this area to include any previous patient condition and hospitals or locations where they might have been treated. The panel B includes an area and a heading to facilitate the listing of a patient's allergies for obvious reasons in a selection or use of a medicine, the same sheet further including a portion identified and used for presenting instructions to a patient or others of use of prescribed medications. The panel C includes areas and identification media headings for a plurality of items of information and also the overall designation of the unit per se, namely "CHEK MED WALLET AND PATIENT EDUCATION PROGRAM". Areas are also designated and usable to include personal information concerning the patient, physician, emergency telephone information and medical insurance information which the patient might have.

The inner faces of the panels or sections, referring to FIG. 4, include on panel A, the heading "Diagnoses"; on panel B, the heading "Medicines"; on the same page, a heading "Diet". The last panel or section is constituted by portions of the article or unit which have been folded upon themselves in such a manner as to provide a pocket, shown in greater detail in FIGS. 4 and 5. The outer face of the interior surface of panel C, designated 10, is adapted for receipt or placement thereon of additional matters of significance or importance to the patient and/or treating person to whom the packet will be available.

The pocket also serves the important function of receiving and maintaining a plurality of cards 14 or the like, a front face of one of which is shown in detail in FIG. 3 and which includes information concerning a particular medicine, identification of the drug and forms thereof as also the uses for this medication and cautions regarding its usage. The opposite card face preferably contains items such as cautions of use, alerting a patient of possible side effects, and additional information of interest in medicament usage by the patient. Obviously a plurality of these cards depending upon prescriptions designated by a treating physician can be placed in the pocket for subsequent reference as to use not only by the patient but also by treating personnel. It is very easy for a user to pull or remove one or more of the cards 14 from the pocket to reveal the information contained thereon.

The uses, functions and desirability of the container and structure of the present invention will be obvious from the foregoing description when taken together with the drawings. A very simple and highly useful article is taught by the invention and which will be of very significant use and interest to the patient as well as persons who subsequently might treat the patient a and utilize the provided information to facilitate the same and avoid difficulties.

Obviously, dimensions and specific structures can be varied as regards materials, designation for inclusion of substantial significance in the conduct and/or treatment subsequently of a patient under normal or emergency conditions.

What is claimed is:

1. A patient medical information and education container, comprising
    an elongated blank including a first pair of spaced parallel fold lines defining first, second, and third panels of similar configurations, each of said panels having factual material designations printed on opposite sides thereof defining area on which factual and medical data relating to a patient is to be placed, said third panel including a pair of side flaps connected therewith and defined by a second pair of spaced parallel fold lines arranged normal to said first pair of fold lines and an end flap connected therewith and defined by a third fold line parallel with said first pair of fold lines, said third panel side flaps being foldable toward each other about said second pair of fold lines, respectively, to positions generally parallel and adjacent said third panel, and said third panel end flap being folded about said third fold line to a position in contiguous relation with said side flaps to define a pocket between said third panel and said side and end flaps; and at least one printed planar card arranged within said pocket, said card having medicinal information for the patient printed on one side thereof and caution information relating to the medicinal information printed on the other side thereof, said panels being successively foldable about said first fold lines into contiguous relation to define a compact container having the general dimensions of one of said panels, whereby said container may easily be carried by a patient in a pocket, wallet, purse, or the like.

2. A container as claimed in claim 1, wherein one of the said panels therefor includes thereon information of possible patient allergies, relating to current medical conditions if any, and any possible conflict with a subsequent medicine suggested to or administered by persons in treatment of a patient.

* * * * *